(12) United States Patent
Hecker et al.

(10) Patent No.: US 8,187,475 B2
(45) Date of Patent: May 29, 2012

(54) METHOD AND APPARATUS FOR PRODUCING AUTOLOGOUS THROMBIN

(75) Inventors: Barry F. Hecker, Pierceton, IN (US); Michael D. Leach, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 442 days.

(21) Appl. No.: 12/399,048

(22) Filed: Mar. 6, 2009

(65) Prior Publication Data

US 2010/0226909 A1 Sep. 9, 2010

(51) Int. Cl.
*B01D 33/15* (2006.01)
*G03C 1/85* (2006.01)

(52) U.S. Cl. ..... 210/782; 210/780; 210/781; 210/380.1; 210/360.1; 210/660; 430/530

(58) Field of Classification Search ................... 210/645, 210/358, 380.1, 767, 319, 660, 210, 173, 210/512.2, 780–782; 422/101, 44; 424/530, 424/529, 531–532, 72
See application file for complete search history.

(56) References Cited

U.S. PATENT DOCUMENTS

| | | |
|---|---|---|
| 3,141,846 A | 7/1964 | Laven, Jr. |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,593,915 A | 7/1971 | Steinacker |
| 3,647,070 A | 3/1972 | Adler |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,897,343 A | 7/1975 | Ayres |
| 3,909,419 A | 9/1975 | Ayres |

(Continued)

FOREIGN PATENT DOCUMENTS

AU 696278 1/1999

(Continued)

OTHER PUBLICATIONS

"Cell Isolation Techniques, Methods and Materials, Working with Enzymes," (2004) (9 pages) Worthington Biochemical Corp.

(Continued)

*Primary Examiner* — Ana Fortuna
(74) *Attorney, Agent, or Firm* — Harness, Dickey (57) ABSTRACT

A device for isolating a component of a multi-component composition. The device includes a housing, a chamber, and a withdrawal port. The chamber is rotatably mounted within the housing. The chamber includes a chamber base and a sidewall. The side wall extends from the chamber base. At least a portion of the sidewall is defined by a filter that permits passage of a first component of the multi-component composition out of the chamber through the filter and to the housing base. The filter restricts passage of a second component of the multi-component composition through the filter. The withdrawal port extends from a position proximate to the housing base to an exterior of the device. The withdrawal port permits the withdrawal of the first component from the housing base to an exterior of the device.

41 Claims, 7 Drawing Sheets

U.S. PATENT DOCUMENTS

| | | | |
|---|---|---|---|
| 3,929,646 A | 12/1975 | Adler | |
| 3,931,010 A | 1/1976 | Ayres et al. | |
| 3,931,018 A | 1/1976 | North, Jr. | |
| 3,935,113 A | 1/1976 | Ayres | |
| 3,941,699 A | 3/1976 | Ayres | |
| 3,972,812 A | 8/1976 | Gresl, Jr. | |
| 3,982,691 A | 9/1976 | Schlutz | |
| 4,001,122 A | 1/1977 | Griffin | |
| 4,046,699 A | 9/1977 | Zine, Jr. | |
| 4,055,501 A | 10/1977 | Cornell | |
| 4,059,108 A | 11/1977 | Latham, Jr. | |
| 4,077,396 A | 3/1978 | Wardlaw et al. | |
| 4,152,270 A | 5/1979 | Cornell | |
| 4,159,896 A | 7/1979 | Levine et al. | |
| 4,187,979 A | 2/1980 | Cullis et al. | |
| 4,204,537 A | 5/1980 | Latham, Jr. | |
| 4,225,580 A | 9/1980 | Rothman et al. | |
| 4,229,298 A | 10/1980 | Bange | |
| 4,269,718 A | 5/1981 | Persidsky | |
| 4,294,707 A | 10/1981 | Ikeda et al. | |
| 4,298,598 A | 11/1981 | Schwarz et al. | |
| 4,300,717 A | 11/1981 | Latham, Jr. | |
| 4,303,193 A | 12/1981 | Latham, Jr. | |
| 4,314,823 A | 2/1982 | Rich, Jr. et al. | |
| 4,322,298 A | 3/1982 | Persidsky | |
| 4,332,351 A | 6/1982 | Kellogg et al. | |
| 4,362,567 A | 12/1982 | Schwarz et al. | |
| 4,364,832 A | 12/1982 | Ballies et al. | |
| 4,377,572 A | 3/1983 | Schwarz et al. | |
| 4,414,976 A | 11/1983 | Schwarz et al. | |
| 4,416,654 A | 11/1983 | Schoendorfer et al. | |
| 4,417,981 A | 11/1983 | Nugent | |
| 4,424,132 A | 1/1984 | Iriguchi et al. | |
| 4,427,650 A | 1/1984 | Stroetmann et al. | |
| 4,427,651 A | 1/1984 | Stroetmann et al. | |
| 4,442,655 A | 4/1984 | Stroetmann et al. | |
| 4,446,021 A | 5/1984 | Aufderhaar et al. | |
| 4,453,939 A | 6/1984 | Zimmerman et al. | |
| 4,464,167 A | 8/1984 | Schoendorfer et al. | |
| 4,537,767 A | 8/1985 | Rothman et al. | |
| RE32,089 E | 3/1986 | Blatt et al. | |
| 4,610,656 A | 9/1986 | Mortensen | |
| 4,617,009 A | 10/1986 | Ohlin et al. | |
| 4,627,879 A | 12/1986 | Rose et al. | |
| 4,631,055 A | 12/1986 | Redl et al. | |
| 4,632,761 A | 12/1986 | Bowers et al. | |
| 4,639,316 A | 1/1987 | Eldegheidy | |
| 4,650,678 A | 3/1987 | Fuhge et al. | |
| 4,655,211 A | 4/1987 | Sakamoto et al. | |
| 4,672,969 A | 6/1987 | Dew | |
| 4,675,117 A | 6/1987 | Neumann et al. | |
| 4,680,025 A | 7/1987 | Kruger et al. | |
| 4,714,457 A | 12/1987 | Alterbaum | |
| 4,722,790 A | 2/1988 | Cawley et al. | |
| 4,724,317 A | 2/1988 | Brown et al. | |
| 4,735,616 A | 4/1988 | Eibl et al. | |
| 4,735,726 A | 4/1988 | Duggins | |
| 4,738,655 A | 4/1988 | Brimhall et al. | |
| 4,755,300 A | 7/1988 | Fischel et al. | |
| 4,755,301 A | 7/1988 | Bowers | |
| 4,770,779 A | 9/1988 | Ichikawa et al. | |
| 4,776,964 A | 10/1988 | Schoendorfer et al. | |
| 4,818,291 A | 4/1989 | Iwatsuki et al. | |
| 4,818,386 A | 4/1989 | Burns | |
| 4,828,710 A | 5/1989 | Itoh et al. | |
| 4,832,851 A | 5/1989 | Bowers et al. | |
| 4,834,890 A | 5/1989 | Brown et al. | |
| 4,839,058 A | 6/1989 | Cawley et al. | |
| 4,844,818 A | 7/1989 | Smith | |
| 4,846,780 A | 7/1989 | Galloway et al. | |
| 4,846,974 A | 7/1989 | Kelley et al. | |
| 4,853,137 A | 8/1989 | Ersson et al. | |
| 4,871,462 A | 10/1989 | Fischel et al. | |
| 4,874,368 A | 10/1989 | Miller et al. | |
| 4,877,520 A | 10/1989 | Burns | |
| 4,879,031 A | 11/1989 | Panzani et al. | |
| 4,900,453 A | 2/1990 | Sedlmayer et al. | |
| 4,902,281 A | 2/1990 | Avoy | |
| 4,928,603 A | 5/1990 | Rose et al. | |
| 4,929,242 A | 5/1990 | Desecki et al. | |
| 4,933,291 A | 6/1990 | Daiss et al. | |
| 4,943,273 A | 7/1990 | Pages et al. | |
| 4,946,601 A | 8/1990 | Fiehler | |
| 4,950,220 A | 8/1990 | Wells et al. | |
| 4,957,638 A | 9/1990 | Smith | |
| 4,983,157 A | 1/1991 | Pober et al. | |
| 4,983,158 A | 1/1991 | Headley | |
| 4,985,153 A | 1/1991 | Kuroda et al. | |
| 5,000,970 A | 3/1991 | Shanbhag et al. | |
| 5,002,571 A | 3/1991 | O'Donnell, Jr. et al. | |
| 5,019,243 A | 5/1991 | McEwen et al. | |
| 5,030,215 A | 7/1991 | Morse et al. | |
| 5,030,341 A | 7/1991 | McEwen et al. | |
| 5,045,048 A | 9/1991 | Kaleskas et al. | |
| 5,053,127 A | 10/1991 | Schoendorfer et al. | |
| 5,071,570 A | 12/1991 | Shiraki et al. | |
| 5,100,564 A | 3/1992 | Pall et al. | |
| 5,104,375 A | 4/1992 | Wolf et al. | |
| 5,112,484 A | 5/1992 | Zuk, Jr. | |
| 5,112,490 A | 5/1992 | Turpen | |
| 5,131,907 A | 7/1992 | Williams et al. | |
| 5,137,832 A | 8/1992 | Levine et al. | |
| 5,141,645 A | 8/1992 | Shiraki et al. | |
| 5,147,290 A | 9/1992 | Jonsson et al. | |
| 5,152,905 A | 10/1992 | Pall et al. | |
| 5,156,613 A | 10/1992 | Sawyer | |
| 5,165,938 A | 11/1992 | Knighton | |
| 5,171,456 A | 12/1992 | Hwang et al. | |
| 5,173,295 A | 12/1992 | Wehling et al. | |
| 5,185,001 A | 2/1993 | Galanakis | |
| 5,188,583 A | 2/1993 | Guigan et al. | |
| 5,190,057 A | 3/1993 | Sarfarazi | |
| 5,190,759 A | 3/1993 | Lindblad et al. | |
| 5,204,537 A | 4/1993 | Bennet et al. | |
| 5,206,023 A | 4/1993 | Hunziker et al. | |
| 5,217,426 A | 6/1993 | Bacehowski et al. | |
| 5,217,627 A | 6/1993 | Pall et al. | |
| 5,219,328 A | 6/1993 | Morse et al. | |
| 5,226,877 A | 7/1993 | Epstein | |
| 5,234,608 A | 8/1993 | Duff | |
| 5,236,604 A | 8/1993 | Fiehler | |
| 5,258,126 A | 11/1993 | Pall et al. | |
| 5,260,420 A | 11/1993 | Burnouf-Radosevich et al. | |
| 5,269,927 A | 12/1993 | Fiehler | |
| 5,271,852 A | 12/1993 | Luoma, II | |
| 5,279,825 A | 1/1994 | Wehling et al. | |
| 5,281,342 A | 1/1994 | Biesel et al. | |
| 5,290,552 A | 3/1994 | Sierra et al. | |
| 5,290,918 A | 3/1994 | Bui-Khac et al. | |
| 5,298,171 A | 3/1994 | Biesel et al. | |
| 5,304,372 A | 4/1994 | Michalski et al. | |
| 5,316,674 A | 5/1994 | Pall et al. | |
| 5,318,524 A | 6/1994 | Morse et al. | |
| 5,318,782 A | 6/1994 | Weis-Fogh et al. | |
| 5,321,126 A | 6/1994 | van Dommelen et al. | |
| 5,322,620 A | 6/1994 | Brown et al. | |
| 5,330,974 A | 7/1994 | Pines et al. | |
| 5,344,752 A | 9/1994 | Murphy | |
| 5,370,802 A | 12/1994 | Brown | |
| 5,376,263 A | 12/1994 | Fischel | |
| 5,387,187 A | 2/1995 | Fell et al. | |
| 5,393,674 A | 2/1995 | Levine et al. | |
| 5,395,923 A | 3/1995 | Bui-Khac et al. | |
| 5,403,272 A | 4/1995 | Deniega et al. | |
| 5,405,607 A | 4/1995 | Epstein | |
| 5,411,885 A | 5/1995 | Marx | |
| 5,417,650 A | 5/1995 | Gordon | |
| 5,420,250 A | 5/1995 | Lontz | |
| 5,443,481 A | 8/1995 | Lee | |
| 5,454,958 A | 10/1995 | Fiehler | |
| 5,456,693 A | 10/1995 | Conston et al. | |
| 5,456,885 A | 10/1995 | Coleman et al. | |
| 5,480,378 A * | 1/1996 | Weis-Fogh et al. | 604/6.04 |
| 5,484,383 A | 1/1996 | Fitch, Jr. et al. | |
| 5,494,578 A | 2/1996 | Brown et al. | |
| 5,494,592 A | 2/1996 | Latham, Jr. et al. | |
| 5,505,685 A | 4/1996 | Antwiler | |

| | | |
|---|---|---|
| 5,510,102 A | 4/1996 | Cochrum |
| 5,533,518 A | 7/1996 | Vogler |
| 5,560,830 A | 10/1996 | Coleman et al. |
| 5,577,513 A | 11/1996 | Van Vlasselaer |
| 5,585,007 A | 12/1996 | Antanavich et al. |
| 5,589,462 A | 12/1996 | Patat et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,905 A | 5/1997 | Haynes |
| 5,641,622 A | 6/1997 | Lake et al. |
| 5,643,192 A | 7/1997 | Hirsh et al. |
| 5,643,193 A | 7/1997 | Papillon et al. |
| 5,674,173 A | 10/1997 | Hlavinka et al. |
| 5,733,545 A | 3/1998 | Hood, III |
| 5,736,033 A | 4/1998 | Coleman et al. |
| 5,762,798 A | 6/1998 | Wenthold et al. |
| 5,788,662 A | 8/1998 | Antanavich et al. |
| 5,795,489 A | 8/1998 | Holm et al. |
| 5,795,571 A | 8/1998 | Cederholm-Williams et al. |
| 5,853,600 A | 12/1998 | McNeal et al. |
| 5,860,937 A | 1/1999 | Cohen |
| 5,889,584 A | 3/1999 | Wardlaw |
| 5,918,622 A | 7/1999 | Perez et al. |
| 5,924,972 A | 7/1999 | Turvaville et al. |
| 5,934,803 A | 8/1999 | Hutter |
| 5,958,253 A * | 9/1999 | Holm ............................ 210/749 |
| 5,980,757 A | 11/1999 | Brown et al. |
| 6,011,490 A | 1/2000 | Tonnesen et al. |
| 6,022,306 A | 2/2000 | Dumont et al. |
| 6,025,201 A | 2/2000 | Zelmanovic et al. |
| 6,027,655 A * | 2/2000 | Holm ............................ 210/749 |
| 6,051,146 A | 4/2000 | Green et al. |
| 6,053,856 A | 4/2000 | Hlavinka |
| 6,054,122 A | 4/2000 | MacPhee et al. |
| 6,063,297 A | 5/2000 | Antanavich et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,153,113 A | 11/2000 | Goodrich et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 * | 4/2001 | Antanavich et al. ....... 424/93.72 |
| 6,245,900 B1 | 6/2001 | Yamasaki et al. |
| 6,274,090 B1 * | 8/2001 | Coelho et al. .............. 435/297.1 |
| 6,277,961 B1 | 8/2001 | Hock et al. |
| 6,280,400 B1 | 8/2001 | Niermann |
| 6,296,602 B1 | 10/2001 | Headley |
| 6,316,247 B1 | 11/2001 | Katz et al. |
| 6,322,785 B1 | 11/2001 | Landesberg et al. |
| 6,334,842 B1 | 1/2002 | Hlavinka et al. |
| 6,342,157 B1 | 1/2002 | Hood, III |
| 6,368,298 B1 | 4/2002 | Beretta et al. |
| 6,464,624 B2 | 10/2002 | Pages |
| 6,472,162 B1 | 10/2002 | Coelho et al. |
| 6,516,953 B1 | 2/2003 | DiCesare et al. |
| 6,544,162 B1 | 4/2003 | Van Wie et al. |
| 6,563,953 B2 | 5/2003 | Lin et al. |
| 6,596,180 B2 * | 7/2003 | Baugh et al. ................... 210/782 |
| 6,629,919 B2 | 10/2003 | Egozy et al. |
| 6,676,629 B2 | 1/2004 | Andrew et al. |
| 6,758,978 B1 | 7/2004 | Bedell |
| 6,764,531 B2 | 7/2004 | Hogan |
| 6,777,231 B1 | 8/2004 | Katz et al. |
| 6,830,762 B2 * | 12/2004 | Baugh et al. ................... 424/530 |
| 6,905,612 B2 | 6/2005 | Dorian et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,179,391 B2 | 2/2007 | Leach et al. |
| 7,694,828 B2 * | 4/2010 | Swift et al. ................. 210/512.3 |
| 7,901,584 B2 * | 3/2011 | Dorian et al. ................. 210/782 |
| 7,987,995 B2 * | 8/2011 | Dorian et al. .............. 210/380.1 |
| 2002/0032112 A1 | 3/2002 | Pages |
| 2002/0076400 A1 | 6/2002 | Katz et al. |
| 2003/0082152 A1 | 5/2003 | Hedrick et al. |
| 2003/0191429 A1 | 10/2003 | Andrew et al. |
| 2004/0171146 A1 | 9/2004 | Katz et al. |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0109716 A1 | 5/2005 | Leach et al. |
| 2005/0153441 A1 | 7/2005 | Hedrick et al. |
| 2005/0153442 A1 | 7/2005 | Katz et al. |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0083720 A1 | 4/2006 | Fraser et al. |
| 2006/0175242 A1 | 8/2006 | Dorian et al. |
| 2006/0175244 A1 | 8/2006 | Dorian et al. |
| 2006/0196885 A1 | 9/2006 | Leach et al. |
| 2006/0243676 A1 * | 11/2006 | Swift et al. ................... 210/782 |
| 2007/0036768 A1 | 2/2007 | Fraser et al. |
| 2007/0075016 A1 | 4/2007 | Leach |
| 2008/0011684 A1 | 1/2008 | Dorian et al. |
| 2008/0283474 A1 | 11/2008 | Leach et al. |
| 2009/0289014 A1 | 11/2009 | Hoeppner |
| 2010/0206798 A1 | 8/2010 | Dorian et al. |
| 2010/0226909 A1 | 9/2010 | Hecker et al. |

FOREIGN PATENT DOCUMENTS

| | | |
|---|---|---|
| BR | 9103724 | 3/1993 |
| CA | 1321138 | 8/1993 |
| CA | 2182862 | 6/1996 |
| CN | 1074709 | 7/1993 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0253198 | 1/1988 |
| EP | 0272915 A2 | 6/1988 |
| EP | 285891 | 10/1988 |
| EP | 0295771 | 12/1988 |
| EP | 0417818 | 3/1991 |
| EP | 0534178 | 3/1993 |
| EP | 0592242 | 4/1994 |
| EP | 1005910 | 6/2000 |
| EP | 1427279 A1 | 6/2004 |
| EP | 1467746 A2 | 10/2004 |
| EP | 1670315 A2 | 6/2006 |
| EP | 1716901 A1 | 11/2006 |
| GB | 854715 | 11/1960 |
| JP | 60-053845 | 3/1985 |
| JP | 60250014 A | 12/1985 |
| JP | 63182055 A | 7/1988 |
| JP | 6454256 | 4/1989 |
| JP | 2036872 | 2/1990 |
| JP | 02071747 | 3/1990 |
| JP | 04500170 T | 1/1992 |
| JP | 6250014 | 9/1994 |
| JP | 09187504 A | 7/1997 |
| JP | 9509432 T | 9/1997 |
| JP | 11502502 T | 3/1999 |
| JP | 2000117150 A | 4/2000 |
| JP | 02129224 | 10/2000 |
| JP | 2001017540 A | 1/2001 |
| JP | 2005523128 T | 8/2005 |
| MX | 246078 | 5/2007 |
| WO | WO-8400905 | 3/1984 |
| WO | WO-8802259 | 4/1988 |
| WO | WO-8901827 A1 | 3/1989 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9616714 A1 | 6/1996 |
| WO | WO-9617871 | 6/1996 |

| | | |
|---|---|---|
| WO | WO-9848938 | 11/1998 |
| WO | WO-0103756 | 1/2001 |
| WO | WO-0183068 | 11/2001 |
| WO | WO-0224107 | 3/2002 |
| WO | WO-03015800 | 2/2003 |
| WO | WO-03024215 A1 | 3/2003 |
| WO | WO-03053362 A2 | 7/2003 |
| WO | WO-03090839 A1 | 11/2003 |
| WO | WO-03092894 A2 | 11/2003 |
| WO | WO-2004009207 | 1/2004 |
| WO | WO-2004037427 A1 | 5/2004 |
| WO | WO-2004104553 A2 | 12/2004 |
| WO | WO-2005034843 A2 | 4/2005 |
| WO | WO-2006081699 A1 | 8/2006 |
| WO | WO-2007142908 A1 | 12/2007 |

OTHER PUBLICATIONS

"Cell Isolation Theory, Tissue Types," (2004) (5 pages) Worthington Biochemical Corp.
"Cytori Celution Cell Concentrate Device," Exhibit 14, 510(k) Summary, FDA approval K060482 (Sep. 28, 2006).
"Frequently Asked Questions, 1. Kits, 2. Engzymes," (2003) 3 pages Worthington Biochemical Corp.
"Sefar Solutions for the Healthcare Industry," brochure (2003) 9 pages Sefar Medifab®.
"Trypsinization of Adherent Cells," (undated) 2 pages.
Anesthesiology, vol. 81, No. 4, pp. 1074-1077, Oct. 1994, Hiromasa Mitsuhata, M.D., et al., "An Anaphylactic Reaction to Topical Fibrin Glue".
Ann Thorac Surg, vol. 53, pp. 530-531, 1992, Mehmet C. Oz, M.D., et al., "Autologous Fibrin Glue From Intraoperatively Collected Platelet-Rich Plasma".
Ann Thorac Surg, vol. 56, pp. 387-389, 1993, Robert L. Quigley, M.D., et al., "Intraoperative Procurement of Autologous Fibrin Glue".
Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (Mar. 1991): 408-11.
Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105(May 1993): 892-7.
Biopolymers, vol. 27, pp. 763-774, 1988, Gerald Marx, "Mechanism of Fibrin Coagulation Based on Selective, Cation-Driven, Protofibral Association".
Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (Jul. 1992): 641-3.
Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 May 1976.
DelRossi, A. J., A. C. Cemaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (Feb. 1990): 281-6.
DeUgarte, M.D., Daniel A., et al., "Future of Fat as Raw Material for Tissue Regneration," (2007) pp. 215-219, Lippincott Williams & Wilkins, Inc.
DiMuzio, Paul et al., "Development of a Tissue-Engineered Bypass Graft Seeded with Stem Cells," Vasucular, vol. 14, No. 6, (2006) pp. 338-342, BC Decker, Inc.
Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".
Edlich, Richard F., George T. Rodeheaver, and John G. Thacker. "Surgical Devices in Wound Healing Management." In *Wound Healing: Biochemical & Clinical Aspects*, ed. I. Kelman Cohen, Robert F. Diegelmann, and William J. Linblad. 581-600. 1st ed., vol. Philadelphia: W.B. Saunders Company, 1992.
Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40-5.
First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.
Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.
Gibble, J. W. and P. M. Ness. "Fibrin glue: the perfect operative sealant?" *Transfusion* 30 (Aug. 1990): 741-7.
Gimble, Jeffrey M., "Adipose-Derived Stem Cells for Regenerative Medicine," Circulation Research (2007) pp. 1249-1260, American Heart Association, Inc.
Gomillion, Cheryl T., et al., "Stem cells and adipose tissue engineering," Biomaterials 27, Science Direct (2006) pp. 6052-6063, Elsevier.
GPS® III System, GPS® III Platelet Separation System, Leadership through Technology, brochure, Jul. 2007 (8 sheets).
GPS® System, "GPS® Platelet Concentrate System," Cell Factor Technologies, Inc., Biomet Orthopaedics, Inc., (2004) (9 pages).
GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.
GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.
GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.
GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.
Guilak, Frank, et al., "Adipose-derived adult stem cells for cartilage tissue engineering," Biorheology 41 (2004) pp. 389-399, IOS Press.
Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.
Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.
Hattori, et al., "Osteogenic Potential of Human Adipose Tissue-Derived Stromal Cells as an Alternative Stem Cell Source," Cells Tissues Organs (2004) 178:2-12 Karger.
Hennis, H. L., W. C. Stewart, and E. K. Jeter. "Infectious disease risks of fibrin glue [letter]." *Ophthalmic Surg* 23 (Sep. 1992): 640.
International Preliminary Report on Patentability mailed Feb. 12, 2009, for PCT/US2007/017055 filed Jul. 31, 2007, which claims benefit of U.S. Appl. No. 60/834,550, filed Jul. 31, 2006, based on U.S. Appl. No. 60/723,312, filed Oct. 4, 2005; U.S. Appl. No. 60/654,718, filed Feb. 17, 2005; and U.S. Appl. No. 60/651,050, filed Feb. 7, 2005.
International Search Report and Written Opinion for PCT/US2006/003597 mailed Feb. 6, 2006.
International Search Report and Written Opinion for PCT/US2006/003599 mailed Aug. 21, 2006.
International Search Report and Written Opinion mailed Aug. 12, 2008 for PCT/US07/17055.
International Search Report and Written Opinion mailed Jul. 3, 2009 for PCT/US2009/035564 claiming benefit of U.S. Appl. No. 61/078,178, filed Jul. 3, 2008.
Jackson, C. M. and Y. Nemerson. "Blood coagulation." *Annu Rev Biochem* 49 (811 1980): 765-811).
Journal of Biomaterials Applications, vol. 7, pp. 309-353, Apr. 1993, David H. Sierra, "Fibrin Sealant Adhesive Systems: A review of their Chemistry, Material Properties and Clinical Appllications".

Journal of Oral Maxillofacial Surgery, vol. 43, pp. 605-611, 1985, Helene Matras, M.D., "Fibrin Seal: The State of the Art".

Kjaergard, H. K,, U. S. Weis-Fogh, H. Sorensen, J. Thiis, and I. Rygg. "A simple method of preparation of autologous fibrin glue by means of ethanol." *Surg Gynecol Obstet* 175 (Jan. 1992): 72-3.

Kjaergard, H. K., Fogh Us Weis, and J. J. Thiis. "Preparation of autologous fibrin glue from pericardial blood." *Ann Thorac Sur* 55 (Feb. 1993): 543-4.

Laryngoscope vol. 99, pp. 974-976, Sep. 1989, Kyosti Laitakari, M.D., et al., "Autologous and Homologous Fibrinogen Sealants: Adhesive Strength".

Laryngoscope, vol. 95, pp. 1074-1076, Sep. 1985, Karl H. Siedentop, M.D., et al., "Autologous Fibrin Tissue Adhesive".

Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".

Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.

Lerner, R. and N. S. Binur. "Current status of surgical adhesives." *J Surg Res* 48 (Feb. 1990): 165-81.

Marrowstim™ Concentration System, (2008) 20 pages Biomet Biologics, Inc.

Matras, Helene, H. P. Dinges, H. Lassmann, and B. Mamoli. "Zur nahtlosen interfaszikularen Nerventransplantation im Tierexperiment." Wein Med Woschtr 122 (37 1972): 517-523.

Moretz, W., Jr., J Shea Jr., J. R. Emmett, and J Shea. "A simple autologous fibrinogen glue for otologic surgery." *Otolaryngol Head Neck Surg* 95 (1 1986): 122-4.

Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.

Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

Otolaryngologic Clinics of North America, vol. 27, No. 1, pp. 203-209, Feb. 1994, Dean M. Toriumi, M.D., et al., "Surgical Tissue Adhesives in Otolaryngology—Head and Neck Surgery".

Parker, Anna M., et al., Adipose-derived stem cells for the regeneration of damaged tissues, Expert Opinion, Cell-& Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.

Plasmax™ Plasma Concentrate, brochure (2006) 5 pages Biomet Biologics, Inc.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.

Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.

Sanal, M. "Does fibrin glue cause foreign body reactions? [letter]." *Eur J Pediatr Surg* 3 (Mar. 1993): 190 (1 page).

Sanal, M., H. Dogruyol, A. Gurpinar, and O. Yerci. "Does fibrin glue cause foreign body reactions?" *Eu r J Pediatr Surg* 2 (May 1992): 285-6.

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.

Sigma-Aldrich® Alkaline Phosphatase (Procedure No. 85), drug fact sheet, (2003) pp. 1-2, Sigma-Aldrich, Inc.

Takahashi, Kazutoshi et al., "Induction of Pluripotent Stem Cells from Adult Human Fibroblasts by Defined Factors," Cell, (2007) pp. 1-12, Elsevier Inc.

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

Vortech™ Concentration System, "Do you want a sticky gel to improve the handling of your bone graft?, Platelet Rich Plasma Concentrate, High Volume in 5 Minutes," Biomet Biologics, Inc., Aug. 2005.

Vox Sanquinis, vol. 68: 82-89, Feb. 1995, Boomgaard Et. al, Pooled Platelet Concentration Prepred by the....

Weis-Fogh, U. S. "Fibrinogen prepared from small blood samples for autologous use in a tissue adhesive system." *Eur Surg Res* 20 (May-Jun. 1988): 381-9.

Wiseman, David M., David T. Rovee, and Oscar M. Alverez. "Wound Dressings: Design and Use." In *Wound Healing: Biochemical & Clinical Aspects*,ed. I. Kelman Cohen, Robert F. Diegelmann, and William J. Lindblad. 562-580. 1st ed., vol. Philadelphia: W.B Saunders Company, 1992).

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

Office Action mailed Sep. 14, 2010 for Japanese Application No. 2007-554193 filed Aug. 23, 2007 has been provided including a partial translation thereof. Japanese Application No. 2007-554193 claims benefit of PCT/US2006/003599, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Office Action mailed Sep. 14, 2010 for Japanese Application No. 2007554191 filed Aug. 7, 2007 has been provided including a partial translation thereof. Japanese Application No. 2007554191 claims benefit of PCT/US2006/003597, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

International Preliminary Examination Report and Written Opinion issued Aug. 31, 2010 for PCT/US2009/035564 claiming benefit of U.S. Appl. No. 61/078,178, filed Jul. 3, 2008 of which U.S. Appl. No. 12/395,085, filed Feb. 27, 2009 claims benefit.

Office Action mailed Apr. 6, 2010 for Japanese Application No. 2007-554193 filed Aug. 23, 2007 has been provided including a partial translation thereof, which cites JP11-502502 and JP2001017540. Japanese Application No. 2007-554193 claims benefit of PCT/US2006/003599, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Office Action mailed Apr. 6, 2010 for Japanese Application No. 2007554191 filed Aug. 7, 2007 has been provided including a partial translation thereof, which also cites JP2001017540. Japanese Application No. 2007554191 claims benefit of PCT/US2006/003597, filed Jan. 30, 2006; claiming priority from U.S. Appl. No. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

"Trypsinizing cells." Bart's Cookbook, Web. Apr. 14, 2010. http://pingu.salk.edu/~sefton/Hyper_protocols/trypsin.html.

DePalma, L., et al., "The preparation of fibrinogen concentrate for use as fibrin glue by four different methods." Transfusion (1993) vol. 33, No. 9; pp. 717-720.

Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.

Hood, Andrew G., et al., "Perioperative Autologous Sequestration III: A New Physiologic Glue with Wound Healing Properties," (Jan. 1993) vol. 14 pp. 126-129.

Longas, Maria O., "An Improved Method for the Purification of Human Fibrinogen." J. Biochem (1980) vol. 11, pp. 559-564.

Marx, Gerard, et al., "Heat Denaturation of Fibrinogen to Develop a Biomedical Matrix." Journal of Biomedical Materials Research Part B: Applied Biomaterials (Apr. 2007) pp. 49-57.

Masri, Marwan A., et al. "Isolation of Human Fibrinogen of High Purity and in High Yield Using Polyethylene Glycol 1000." Thromb Haemostas (Stuttgart) (1983) vol. 49 (2); pp. 116-119.

Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).

Silver, Frederick H., et al., "Review Preparation and use of fibrin glue in surgery." Biomaterials 16 (1995) pp. 891-903.

Solem, Jan Otto, et al., "Hemoconcentration by Ultrafiltration During Open-Heart Surgery," Scand J Thor Cardiovasc Surg 22:271-274, 1988.

Sutton, Robin G., et al. "Comparison of Three Blood-Processing Techniques During and After Cardiopulmonary Bypass." Ann Thorac Surg (1993) vol. 56; pp. 941-943.

Weisman, MD., Robert A., "Biochemical Characterization of Autologous Fibrinogen Adhesive," Laryngoscope 97: Oct. 1987; pp. 1186-1190.

* cited by examiner

METHOD AND APPARATUS FOR PRODUCING AUTOLOGOUS THROMBIN

FIELD

The present disclosure relates to methods and devices for isolating components of a multi-component composition, such as isolating thrombin from whole blood or plasma.

BACKGROUND

The statements in this section merely provide background information related to the present disclosure and may not constitute prior art.

Thrombin, which is found naturally in whole blood, plays an important role in the blood clotting process. Specifically, thrombin is an enzyme of blood plasma that catalyzes the conversion of fibrinogen to fibrin, the last block of the blood clotting process. Thus, the clotting process can be enhanced by isolating fibrinogen and thrombin from whole blood or plasma and introducing increased amounts of these blood components to a wound site. While current methods and devices for isolating thrombin are suitable for their intended use, they are subject to improvement.

SUMMARY

The present teachings provide for a device for isolating a component of a multi-component composition. The device includes a housing, a chamber, and a withdrawal port. The chamber is rotatably mounted within the housing. The chamber includes a chamber base and a sidewall. The side wall extends from the chamber base. At least a portion of the sidewall is defined by a filter that permits passage of a first component of the multi-component composition out of the chamber through the filter and to the housing base. The filter restricts passage of a second component of the multi-component composition through the filter. The withdrawal port extends from a position proximate to the housing base to an exterior of the device. The withdrawal port permits the withdrawal of the first component from the housing base to an exterior of the device.

The present teachings further provide for a method for isolating thrombin from a multi-component composition. The method includes the following: loading the composition into a chamber rotatably mounted in a housing, the chamber including glass beads and polyacrylimide beads; loading reagent into the chamber; rotating the chamber at a first speed for a first time period to mix the contents of the chamber and form a mixture; rotating the chamber at a second speed for a second time period to cause thrombin to separate from the mixture and pass through a filter of the chamber and collect outside of the chamber; and extracting the thrombin from within the housing.

The present teachings further provide for a method for isolating thrombin from a multi-component composition. The method includes the following: forming a solution including about 24 cc of the composition, about 8 grams of glass beads, about 4.5 grams of polyacrylimide beads, and about 8 cc of reagent; mixing the solution for about one minute at about 50 rpm; and rotating the solution at a speed of from about 1,500 rpm to about 3,500 rpm for about two minutes to separate thrombin from the solution.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
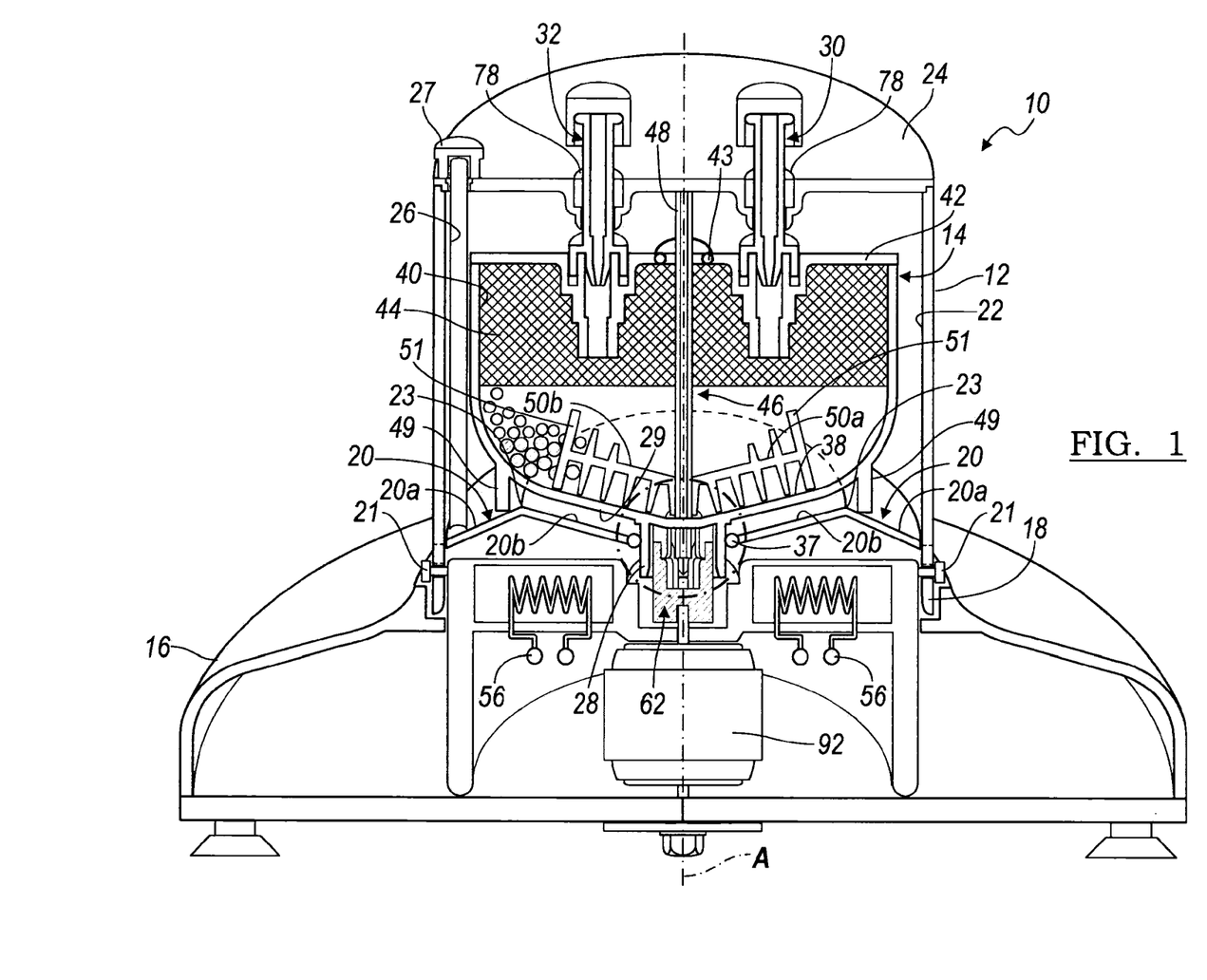
FIG. 1 is a cross-sectional view of a component isolation device according to the present teachings seated on a torque generating device.
Figure 2:
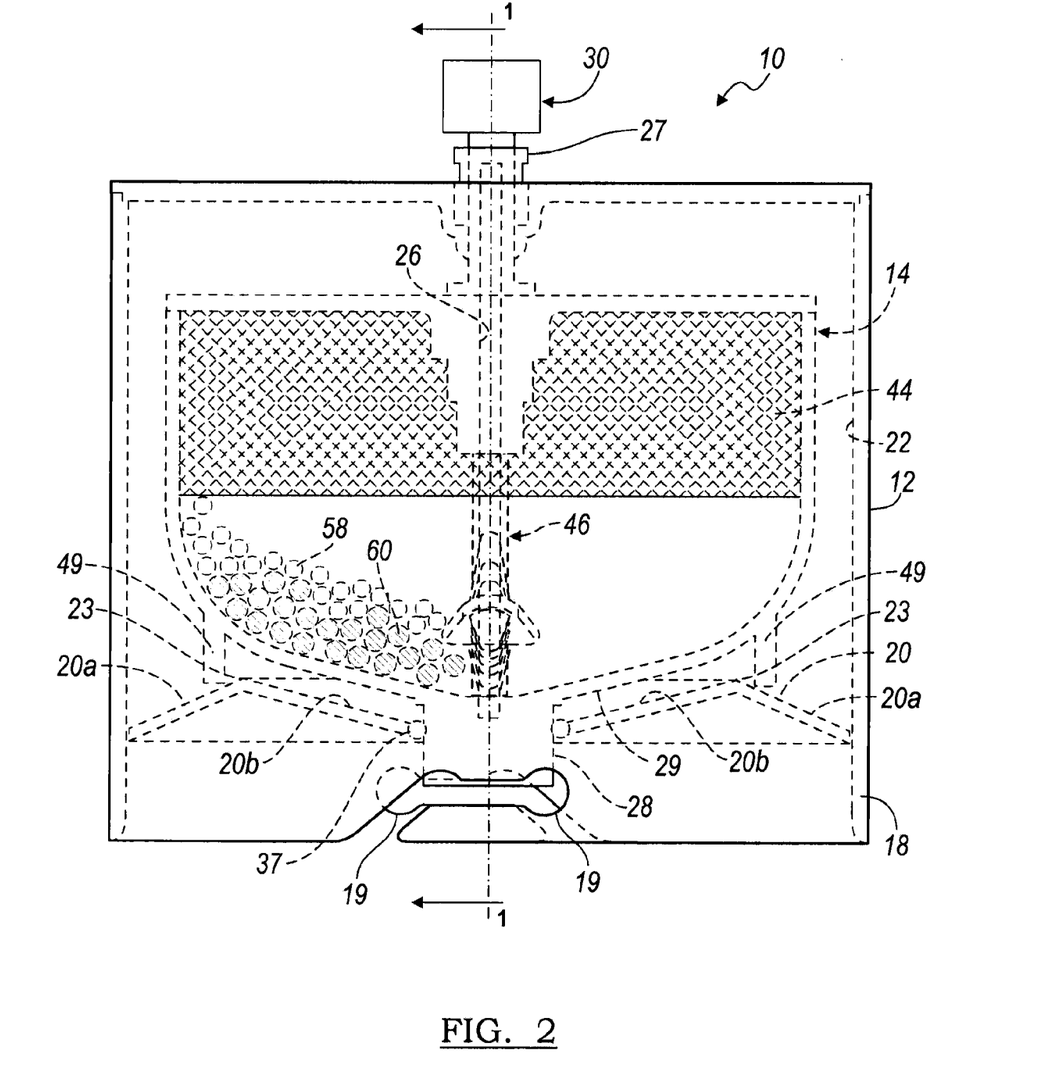
FIG. 2 is a side view of the component isolation device of FIG. 1.
Figure 3:
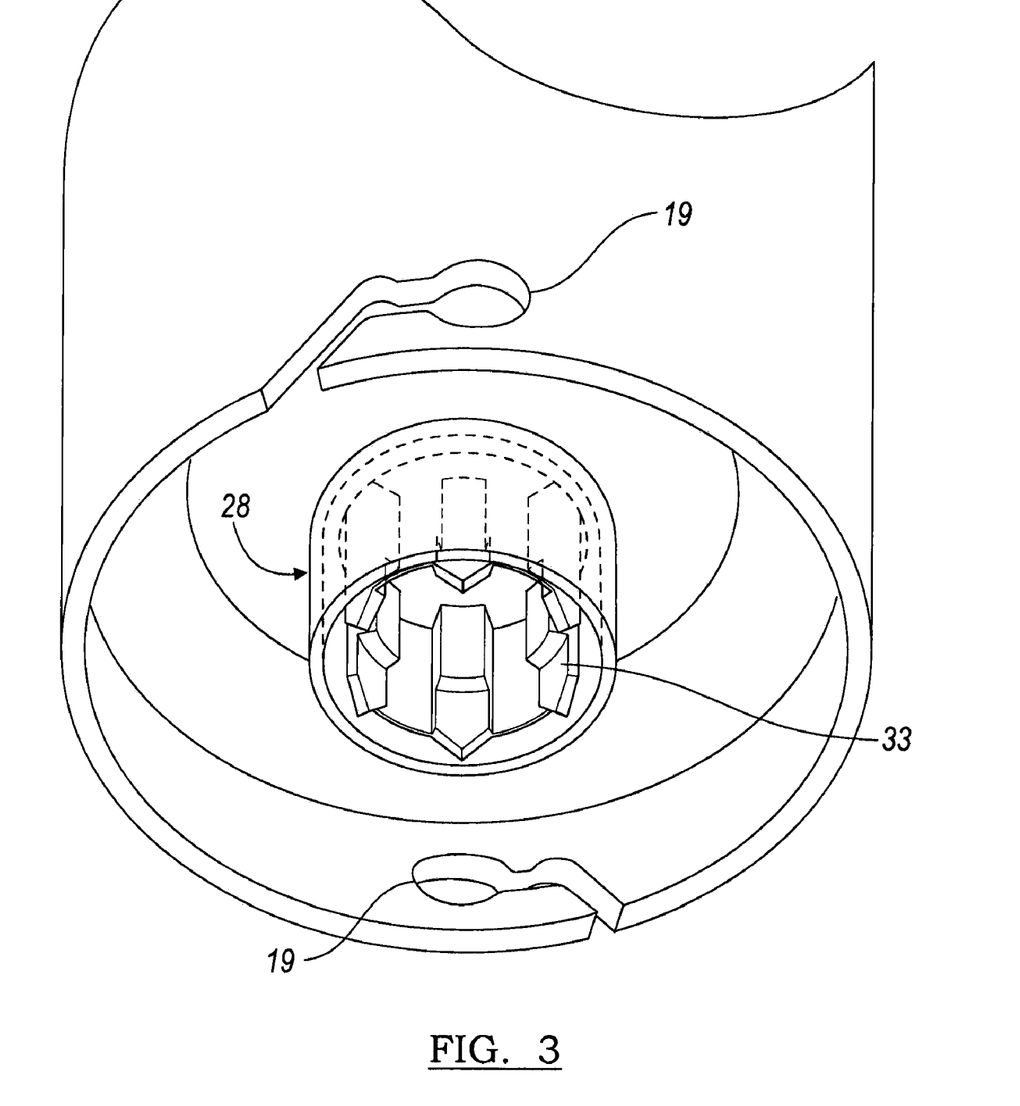
FIG. 3 is a bottom perspective view of the component isolation device of FIG. 1.

With initial reference to FIGS. 1-3, a device for isolating one or more components of a multi-component composition is illustrated at reference numeral 10. The device 10 generally includes a housing 12 and a chamber 14 rotatably mounted within the housing 12. The chamber 14 is generally cylindrical and is rotated by a torque generating device 16.

The housing 12 generally includes a substantially cylindrical support portion 18, a base portion 20, a sidewall 22, a cover 24, an aspiration port 26, and an axially concentric drive receptor 28.

The cylindrical support portion 18 extends from the base portion 20. The cylindrical support portion 18 includes a pair of locking slots 19. The locking slots 19 (see FIG. 2) cooperate with tabs 21 of the torque generating device 16 to secure the housing 12 to the torque generating device 16.

The base portion 20 is between the sidewall 22 and the support portion 18. The base portion 20 includes a first sloped portion 20a and a second sloped portion 20b. The first sloped portion 20a is proximate to the sidewall 22 and slopes toward the sidewall 22. The second sloped portion 20b is distal to the sidewall 22 and extends to an axis of rotation A of the chamber 14. The second sloped portion 20b slopes away from the sidewall 22. The first sloped portion 20a meets the second sloped portion 20b at an apex portion 23. The first sloped portion 20a directs materials deposited on the first sloped portion 20a toward the sidewall 22 where the materials can be removed from the device 10 through the aspiration port 26.

The drive receptor 28 extends from an under surface 29 of the chamber 14 along the axis of rotation A of the chamber 14. The drive receptor is mounted to the base portion 20 with one or more bearings 37 to permit the chamber 14 to rotate within the housing 12. The drive receptor 28 can be any suitable device for cooperating with the torque generating device 16 to transfer torque from the device 16 to the chamber 14. For example and with reference to FIG. 3, the drive receptor 28 includes an outer cylinder 31 and a series of pointed prongs 33 within the outer cylinder 31. The prongs 33 are sized and shaped to cooperate with a motor connector 62 of the torque generating device 16.

The cover 24 is mounted to an end of the sidewall 22 opposite to the base portion 20. In some applications, the cover 24 is removable. A first inlet subassembly 30 and a second inlet subassembly 32 extend through openings in the cover 24 to provide fluid communication through the cover 24 into the chamber 14. The inlet subassemblies 30 and 32 can be any suitable type of inlet or port and are further described herein.

The aspiration port 26 extends through the cover 24 to a point proximate to the base portion 20. The aspiration port 26 is proximate to the sidewall 22 and extends parallel to the sidewall 22. The aspiration port 26 includes a removable aspiration cap 27.

The chamber 14 includes a chamber base 38, a generally cylindrical chamber sidewall 40 extending from the chamber base 38, and a chamber cover 42. A portion of the chamber sidewall 40 proximate to the chamber cover 42 includes a filter 44 having numerous openings. The filter 44 extends around the cylindrical chamber sidewall 40. The filter 44 can be mounted to the sidewall 40 in any suitable manner, such as with ultrasonic welding.

The filter 44 can be any suitable filter capable of permitting the passage of the components of the multi-composition that are desired for collection through the aspiration port 26 and restricting passage of other materials. For example, the filter 44 can be made of a fabric that is cross woven to form openings in the fabric.

Suitable fabrics can include polyester, such as polyethylene terephthalate (PET). An exemplary filtration fabric for use in filter 44 includes Sefar Medifab® product number 07-15/9 by Sefar, Inc. of Ruschlikon, Switzerland. This product is made of PET monofilament and includes the following properties: a weave pattern of about 2:2 twill weave; a mesh opening having a width of about of 15 μm, +/−2.0 μm; a mesh count of about 194.0 n/cm (n/cm=10,000/(mesh opening+ wire diameter)); a wire diameter of about 37 μm; an open area of about 8.5% (($a_o$) [%]=(w)$^2$×100/(w+d)$^2$); a thickness of about 55 μm; a weight of about 45 g/m$^2$; and a medical washed finish.

A mixing paddle 46 is mounted within the chamber 14. The mixing paddle 46 includes a main portion 48 and a branched portion 50. The main portion 48 is mounted to the cover 24. The main portion 48 extends through an opening in the chamber cover 42 to within the chamber 14 to a point proximate to the chamber base 38. The branched portion 50 includes two extending portions 50a and 50b that extend from the main portion 48 and are positioned at 180° to each other. The extending portions 50a and 50b extend at an angle so that they are always proximate to the chamber base 38, which slopes upward from the axis of rotation A. The extending portions 50a and 50b each include fins 51 that protrude from the extending portions 50a and 50b at right angles.

The mixing paddle 46 is fixedly mounted to the cover 24 such that it remains stationary to mix the contents of the chamber 14 when the chamber 14 is rotating. A bearing 43 is between the chamber cover 42 and the main portion 48 to permit the chamber cover 42 to rotate about the main portion 48.

An annular rim 49 extends from the undersurface 29 of the chamber base 38. The annular rim 49 is positioned proximate to the apex portion 23 between the apex portion 23 and the sidewall 22. The annular rim 49 prevents material exiting the chamber 14 through the filter 44 from passing over the apex portion 23 to the second sloped portion 20b. The annular rim 49 keeps material exiting the chamber 14 on the first sloped portion 20a, whereby the material can be withdrawn through the aspiration port 26.

Figure 4:
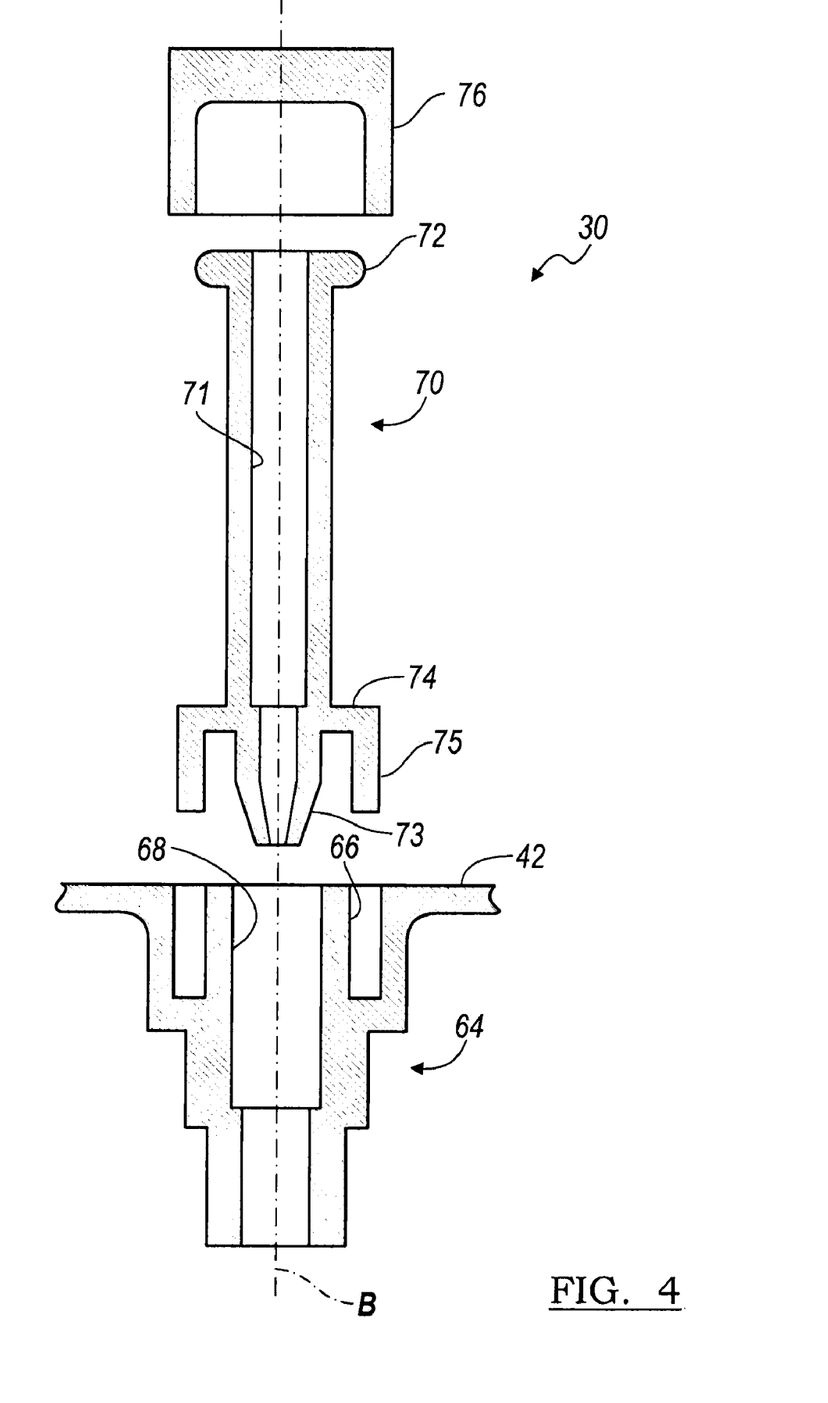
FIG. 4 is a cross-sectional view of an inlet subassembly of the component isolation device of FIG. 1.

With additional reference to FIG. 4, the first inlet assembly 30 includes an inlet tube 64 provided in the chamber cover 42. The inlet tube 64 includes an annular receptor 66. The inlet tube 64 defines a passageway 68 through the chamber cover 42. A sterile filter (not shown) can be positioned in the passageway 68 of the inlet tube 64. The sterile filter can be any suitable filter for preventing the passage of undesirable materials, such as contaminants, beads, clotted portions of blood, etc. For example, the filter can be a syringe filter having openings sized between about 40 and about 100 microns. The passageway 68 can further include a seal (not shown) to prevent contaminants from passing into the chamber 14. The seal can be penetrable to permit introduction of materials into the chamber 14, such as by a syringe used to load the reagent or blood into the chamber 14.

The inlet assembly 30 further includes a removable inlet tube 70 that defines a through bore 71. The removable tube 70 includes an integral Luer fitting 72 at a first end and a tapered portion 73 at a second end opposite to the first end. Proximate to the second end is a plate 74 extending outward from the removable inlet tube 70. The plate 74 extends approximately perpendicular to a longitudinal axis B of the through bore 71. An integral cylindrical flange 75 extends perpendicular to the plate 74. The cylindrical flange 75 is sized to engage the annular receptor 66. The inlet assembly 30 further includes a cap 76 that cooperates with the Luer fitting 72 to provide a sterile closure of the removable tube 70 prior to use, such as during shipment and handling.

As illustrated in FIGS. 1 and 2, prior to use, the removable tube 70 is positioned such that it extends through an opening 78 in the cover 24 of the housing 12 and through the inlet tube 64 of the chamber cover 42 so that the through bore 71 provides a passageway from the exterior of the device 10 to within the chamber 14. In particular, the removable tube 70 is positioned such that the flange 75 is seated within the annular receptor 66 of the chamber cover 42. The removable tube 70, in passing through both the cover 24 and the chamber cover 42, locks the chamber 14 in position and prevents the chamber 14 from rotating during shipment and storage. After a multicomponent composition is introduced into the chamber 14 through the first inlet assembly 30, the removable tube 70 is removed, thereby unlocking the chamber 14 to permit the chamber 14 to rotate about the axis of rotation A. The second inlet assembly 32 is substantially similar to the first inlet assembly 30. Therefore, the above description of the first inlet assembly 30 also applies to the second inlet assembly 32.

Figure 5:
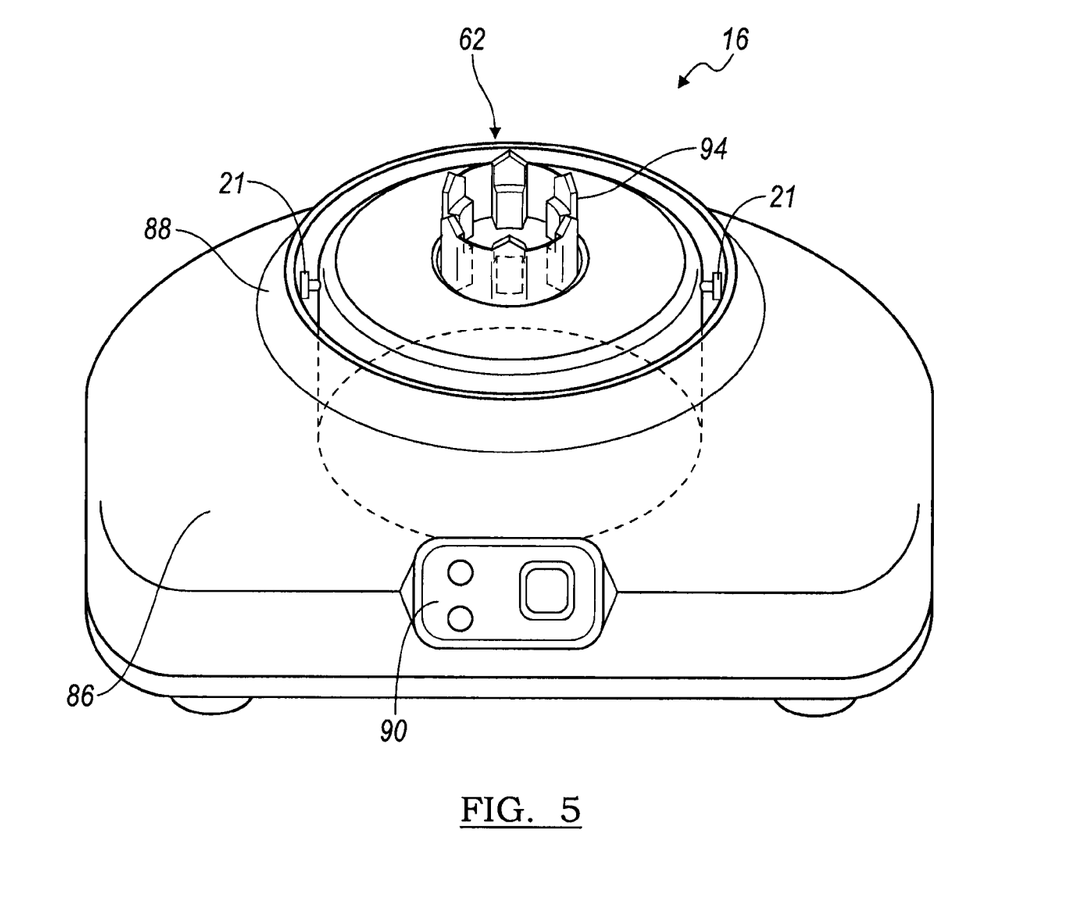
FIG. 5 is a top perspective view of the torque generating device.

With additional reference to FIG. 5, the torque generating device 16 can be any suitable torque generating device. For example, the torque generating device 16 can be a Vortech® base by Biomet Biologics, LLC of Warsaw, Ind., such as disclosed in United States Patent Publication No. 2006/0175244 (application Ser. No. 11/342,749) filed on Jan. 30, 2006, which is hereby incorporated by reference. As illustrated, the torque generating device 16 includes a base 86 having a raised annular support surface 88 and a control panel 90. At a center of the raised annular support surface 88 is the motor connector 62 that is connected to a motor 92 (FIG. 1) of the torque generating device 16. The motor connector 62 is rotated by the motor 92. The motor 92 is controlled using the control panel 90. The motor connector 62 includes a plurality of receptors 94 that cooperate with the prongs 33 of the drive receptor 28 to transfer torque generated by the motor to the drive receptor 28 to rotate the chamber 14.

The torque generating device 16 further includes a heater 56 (FIG. 1). The heater 56 is used to heat the contents of the chamber 14. The heater 56 can be any suitable heater, such as an induction heater, a conduction heater, or an infra-red heater. When the heater 56 is an induction heater, a metal insert can be positioned at the bottom of the chamber 14 and the torque generating device 16 can include a heating coil to conduct current between the device 16 and the chamber 14 to heat the metal insert and ultimately the chamber 14 and its contents.

The device 10 can be used to isolate components of a variety of multi-component compositions. For example, the device 10 can be used to isolate thrombin from whole blood and thrombin from plasma, including platelet rich plasma and platelet rich plasma concentrate.

Figure 6:
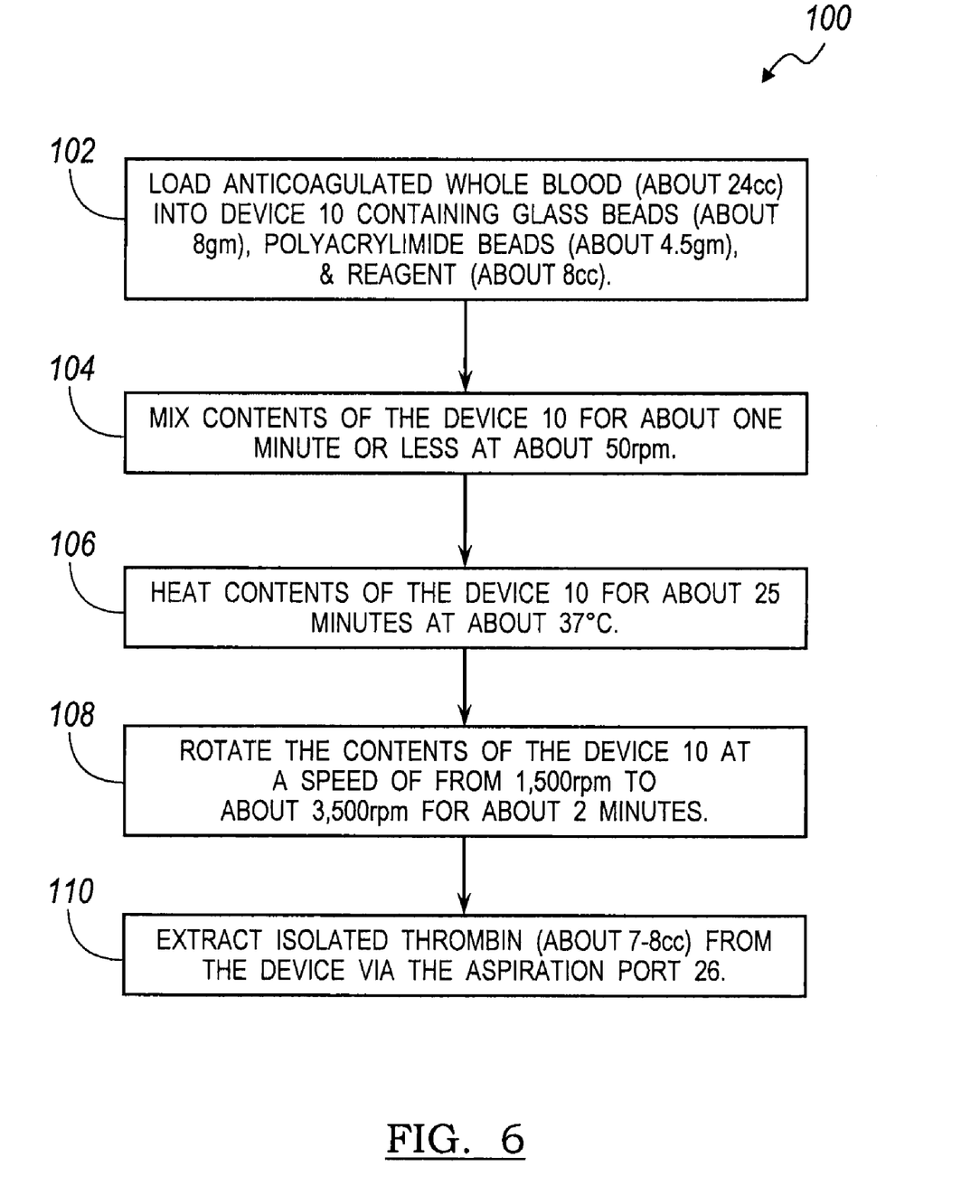
FIG. 6 illustrates a method according to the present teachings for isolating thrombin from whole blood.

With additional reference to FIG. 6, a method for isolating thrombin from whole blood according to the present teachings is at reference number 100. With initial reference to block 102, a suitable amount of anticoagulated whole blood, either autologous or nonautologous, is loaded into the chamber 14 of the device 10. Any suitable amount of whole blood can be used, such as about 24 cc. The blood is loaded through the first inlet assembly 30. A suitable reagent, such as a calcium based compound, is also loaded into the chamber 14. The reagent can include any suitable calcium based compound with or without a suitable alcohol. An exemplary suitable reagent includes calcium chloride and ethanol.

The reagent is loaded through the second inlet assembly 32. Any suitable amount of reagent can be used, such as about 8 cc. The presence of the first and the second inlet assemblies 30 and 32 is advantageous because it provides for a more aseptic process whereby the seal of each of the inlet assemblies is only penetrated once.

To facilitate activation of blood platelets, glass beads 58 are included in the chamber 14. Polyacrylimide beads 60 are also included in the chamber 14. The beads 58 and 60 are typically loaded into the chamber 14 by the manufacturer. Any suitable amount of glass beads 58 and polyacrylimide beads 60 can be used, such as about 8 grams of glass beads and about 4.5 grams of polyacrylimide beads. After the whole blood and reagent are loaded into the chamber 14, the removable tubes 70 are removed from the first and the second inlet assemblies 30 and 32 to permit the chamber 14 to rotate freely within the housing 12.

At block 104, the whole blood, the glass beads 58, the polyacrylimide beads 60, and the reagent, which are all present in the chamber 14, are mixed. The contents of the chamber 14 are mixed by placing the device 10 on the annular support surface 88 of the torque generating device 16. Torque generated by the torque generating device 16 is transferred to the chamber 14 through the interaction between the motor connector 62 and the drive receptor 28 to rotate the chamber 14. The chamber 14 is rotated for about one minute or less at about 50 rpm. The fixed mixing paddle 46 present in the chamber 14 facilitates mixing of the contents of the chamber 14.

At block 106, the contents of the chamber 14 are optionally heated or incubated by the heater 56 for about 25 minutes at about 37° C. The incubation process causes the red blood cells of the whole blood to activate and form a clot, thereby releasing thrombin. After the incubation process, the chamber 14 is rotated at a speed of from about 1,500 rpm to about 3,500 rpm for about 2 minutes at block 108 to separate the contents. The polyacrylimide beads 60 remove excess water from the mixture to increase the concentration of thrombin. For example, use of 4.5 grams of polyacrylimide beads 60, which is more than is typically used, can result in isolation of thrombin that is concentrated at six to seven times.

The rotation at an increased speed (block 108) causes thrombin to separate from the mixture and rise to the area of the filter 44. The openings of the filter 44 are sized to permit the passage of thrombin through the filter 44. The openings of the filter 44 are not large enough to permit the glass beads 58 and polyacrylimide beads 60 to pass through the filter 44. Therefore, the glass beads 58 and the polyacrylimide beads 60 remain within the chamber 14.

Thrombin passes through the filter 44 and settles outside of the chamber 14 on the first sloped portion 20a of the base portion 20. The thrombin can slide down the sidewall 22 to reach the first sloped portion 20a. Due to the presence of the annular rim 49 and because the first sloped portion 20a is sloped toward the sidewall 22, the thrombin is directed toward the sidewall 22 where it can be extracted from the device 10 through the aspiration port 26. At block 110, thrombin can then be extracted through the aspiration port 26 using any suitable device, such as a syringe. Typically, about 7-8 cc of thrombin can be extracted. Thus, the method 100 isolates thrombin of increased concentration from autologous or non-autologous whole blood. As set forth below, the isolated thrombin can be used in a variety of ways to enhance the blood clotting and healing process.

Figure 7:
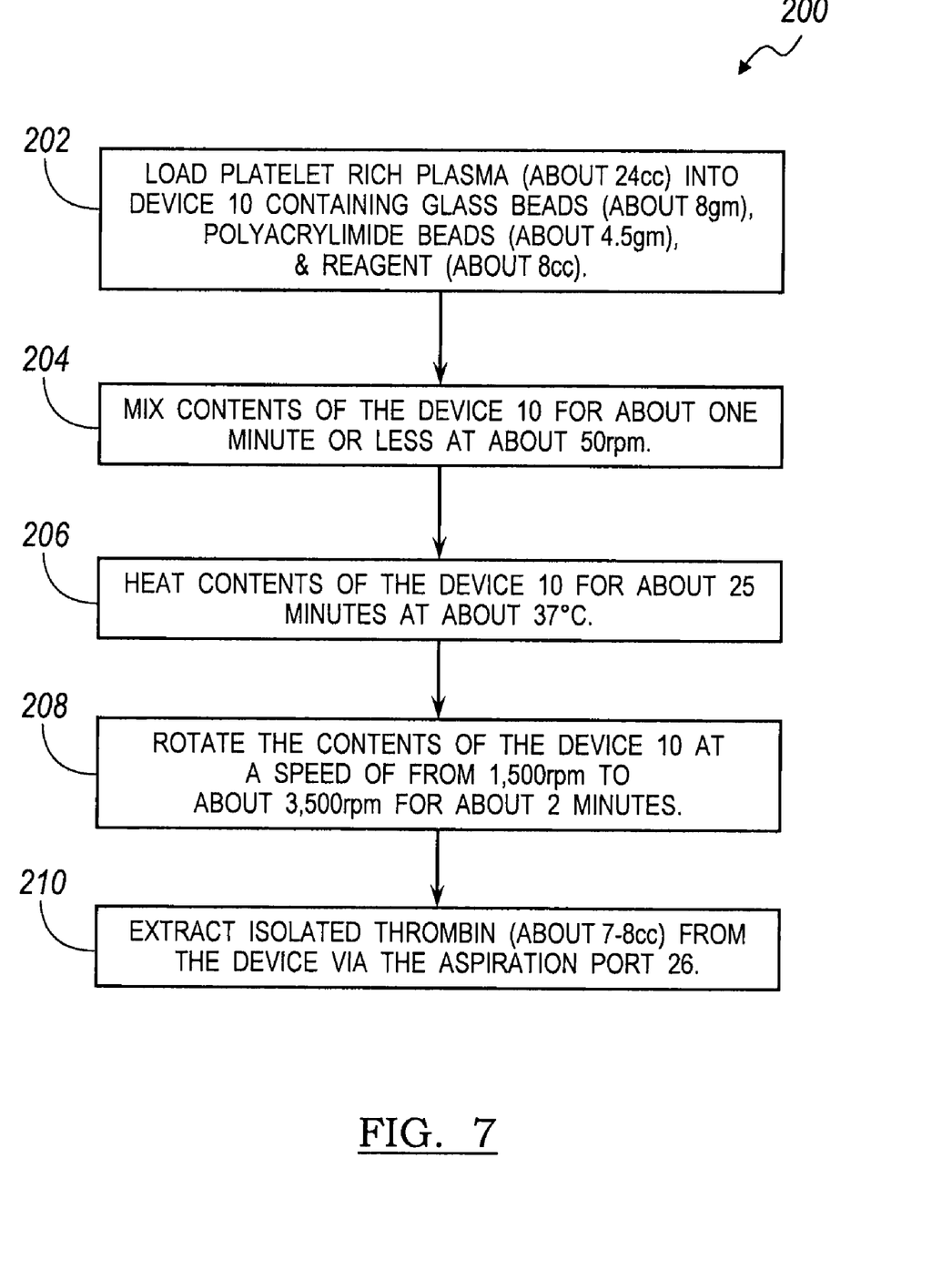
FIG. 7 illustrates a method according to the present teachings for isolating thrombin from platelet rich plasma.

With additional reference to FIG. 7, an additional method for isolating thrombin according to the present teachings will be described. With initial reference to block 202, a suitable amount of platelet rich plasma concentrate is loaded into the chamber 14 of the device 10. Any suitable amount of platelet rich plasma concentrate can be used, such as about 24 cc. The platelet rich plasma concentrate can be obtained using any suitable method or device, such as the device disclosed in United States Patent Publication No. 2006/0175244 (application Ser. No. 11/342,749) filed on Jan. 30, 2006, the Plasmax Plasma Concentrate Kit™ or the Vortech Concentration System™, all sold by Biomet Biologics, LLC of Warsaw, Ind. The platelet rich plasma concentrate can be isolated from autologous or non-autologous blood. The platelet rich plasma is loaded through the first inlet assembly 30. A suitable reagent, such as a calcium chloride and ethanol solution, is loaded into the chamber 14. The reagent is loaded through the second insert assembly 32.

Glass beads 58 and polyacrylimide beads 60 are included in the chamber 14. The beads 58 and 60 are typically loaded into the chamber 14 by the manufacturer. Any suitable amount of glass beads 58 and polyacrylimide beads 60 can be used, such as about 8 grams of glass beads and about 4.5 grams of polyacrylimide beads. The glass beads 58 facilitate activation of the blood platelets. After the whole blood and reagent are loaded into the chamber 14, the removable tubes 70 are removed from the first and the second inlet assemblies 30 and 32 to permit the chamber 14 to rotate freely in the housing 12.

At block 204, the platelet rich plasma, the glass beads 58, the polyacrylimide beads 60, and the reagent, which are all present in the chamber 14, are mixed. The contents of the chamber 14 are mixed by placing the device 10 on the annular support surface 88 of the torque generating device 16. Torque generated by the torque generating device 16 is transferred to the chamber 14 through the interaction between the motor connector 62 and the drive receptor 28 to rotate the chamber 14. The mixing paddle 46 facilitates mixing of the contents of the chamber 14. The presence of the glass beads 58 during rotation of the chamber 14 facilitates activation of the platelets.

At block 206, the contents of the chamber 14 are optionally heated or incubated by the heater 56 for about 25 minutes at about 37° C. The incubation process further activates the platelets to form a clot, thereby releasing thrombin. After the incubation process, the contents of the chamber 14 are rotated at a speed of from about 1,500 rpm to about 3,500 rpm for about 2 minutes at block 208. The polyacrylimide beads 60 remove excess water from the mixture to increase the concentration of thrombin provided. For example, use of about 4.5 grams of polyacrylimide beads 60 can result in thrombin that is about 6-7 times more concentrated than thrombin obtained without using such a quantity of polyacrylimide beads 60.

The rotation at an increased speed (block 208) causes thrombin to separate from the mixture and rise to the area of the filter 44. As set forth above, the filter 44 is sized to permit passage of the thrombin, but not other components of the mixture, such as the glass beads 58 and the polyacrylimide beads 60. The thrombin settles on the first portion 20a of the base portion 20 where it can be withdrawn from the device 10 through the aspiration port 26 using any suitable device, such as a syringe, at block 210. About 7-8 cc of thrombin can be obtained from about 24 cc of platelet rich plasma concentrate. Thus, the method 200 isolates thrombin that is of an increased concentration, such as about 6-7 times more concentrated, from platelet rich plasma derived from autologous or non-autologous blood. As set forth below, the isolated thrombin can be used in a variety of different ways to enhance the clotting and healing process.

The isolated thrombin can be used for a variety of different purposes. For example, the isolated thrombin can be loaded into a suitable sprayer device along with platelet poor plasma and introduced to a wound at a ratio of from about 5:1 to about 10:1 [thrombin to platelet poor plasma] to facilitate wound healing. The introduction of such a mixture to a wound facilitates clotting in as little as 15 seconds. The clotting process is expedited due to the presence of thrombin of increased concentration.

The isolated thrombin may also be used as a hemostatic agent and added directly to a wound or surgical site to enhance healing. Further, the isolated thrombin can be added to platelet gels, fibrin glues, plasma (platelet rich and platelet poor) to enhance their wound healing properties. For example, the isolated thrombin can be added to the plasma output of the Plasmax Plasma Concentrate Kit™ by Biomet Biologics, LLC of Warsaw, Ind.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method for isolating thrombin from a multi-component composition comprising:
   loading the composition into a chamber rotatably mounted in a housing, the chamber including glass beads and polyacrylimide beads;
   loading reagent into the chamber;
   rotating the chamber at a first speed for a first time period to mix the contents of the chamber and form a mixture;
   rotating the chamber at a second speed for a second time period to cause thrombin to separate from the mixture, rise to a filter of the chamber, pass through the filter of the chamber, and collect outside of the chamber between an inner wall of the housing and the chamber to facilitate collection of the thrombin; and
   extracting the thrombin from within the housing.

2. The method of claim 1, further comprising heating the mixture to facilitate release of thrombin from the mixture.

3. The method of claim 1, wherein the composition includes whole blood.

4. The method of claim 1, wherein the composition includes plasma.

5. The method of claim 1, further comprising loading about 24 cc of one of whole blood or plasma into the chamber.

6. The method of claim 5, wherein said mixture is heated at about 37° C. for about 25 minutes to activate red blood cells of the mixture to from a clot and release thrombin.

7. The method of claim 1, wherein the chamber includes about 8 grams of glass beads.

8. The method of claim 1, wherein the chamber includes about 4.5 grams polyacrylimide beads.

9. The method of claim 1, further comprising loading about 8 cc of the reagent into the chamber, the reagent comprising calcium chloride and ethanol.

10. The method of claim 1, wherein said first speed is about 50 rpm and said first time period is about one minute to mix the contents of the chamber.

11. The method of claim 10, wherein said second speed is from about 1,500 rpm to about 3,500 rpm and said second time period is about two minutes to separate the components of the mixture including separating thrombin from a blood clot.

12. The method of claim 1, further comprising:
   fixedly coupling the housing to a torque generating device in a nonrotatable manner; and
   coupling the chamber to a motor connector of the torque generating device such that upon activation of a motor of the base the chamber is rotated within the housing and independent of the housing about an axis of rotation of the chamber.

13. The method of claim 12, wherein coupling the chamber to the motor connector includes interconnecting prongs of a drive receptor of the housing and chamber with spaced apart receptors of the motor connector.

14. The method of claim 13, further comprising orientating the chamber such that the axis of rotation of the chamber is aligned with an axial center of both the motor connector and the drive receptor.

15. The method of claim 12, further comprising extracting the thrombin through an aspiration port fixedly mounted between the inner wall of the housing and the chamber.

16. The method of claim 12, further comprising loading the composition into the chamber through an inlet subassembly including an inlet tube fixedly mounted to a cover of the chamber and a removable tube removably coupled to the inlet tube;
   wherein the removable tube is coupled to the inlet tube and the chamber cover during loading of the composition into the chamber, and decoupled from the chamber cover and the inlet tube after loading to permit rotation of the chamber within the housing.

17. A method for isolating thrombin from a multi-component composition comprising:
   fixedly attaching a housing with a single chamber rotatably mounted therein to a torque generating device, the chamber including an axis of rotation extending through an axial center of the chamber;
   coupling the chamber to the torque generating device such that upon activation of a motor of the torque generating device the chamber is rotated within the housing about the axis of rotation of the chamber;

forming a solution in the chamber, the solution including the following:
- about 24 cc of the multi-component composition;
- about 8 grams of glass beads;
- about 4.5 grams of polyacrylimide beads; and
- about 8 cc of reagent;

mixing the solution for about one minute at a speed of about 50 rpm bar rotating the chamber about the axis of rotation of the chamber without rotating the housing; and rotating the solution at a speed of from about 1,500 rpm to about 3,500 rpm for about two minutes to separate thrombin from the solution through a filter in the chamber by rotating the chamber about the axis of rotation of the chamber without rotating the housing.

18. The method of claim 17, further comprising heating the solution for about 25 minutes at about 37° C. to facilitate release of thrombin from the multi-component composition.

19. The method of claim 17, further comprising:
isolating about 7 cc to about 8 cc of thrombin.

20. The method of claim 17, wherein the thrombin is concentrated at from about 6× to about 7×.

21. The method of claim 17, wherein the thrombin can be applied to a wound site.

22. The method of claim 17, further comprising forming a second solution that includes about ten parts thrombin and about one part platelet poor plasma wherein the second solution can be applied to a wound.

23. The method of claim 22, wherein the second solution can be sprayed onto the wound.

24. The method of claim 17, wherein said multi-component composition includes whole blood.

25. The method of claim 17, wherein said multi-component composition includes concentrated platelet rich plasma.

26. The method of claim 17, wherein said multi-component composition includes plasma.

27. The method of claim 17, wherein the solution is rotated at about 1,500 rpm to about 3,500 rpm for about two minutes to cause the thrombin to rise to a filter of the chamber, pass through the filter, and collect outside the chamber between an inner wall of the housing and the chamber to facilitate collection of the thrombin.

28. The method of claim 27, further comprising extracting the thrombin from the chamber through an aspiration port fixedly mounted between an inner wall of the housing and the chamber.

29. The method of claim 17, wherein coupling the chamber to the torque generating device includes coupling interconnecting prongs of a drive receptor of the chamber with spaced apart receptors of a motor connector of the torque generating device.

30. A method for isolating thrombin from a multi-component composition comprising:

loading the composition into a single chamber rotatably mounted in a housing fixedly coupled to a torque generating base, the chamber including an axis of rotation extending through an axial center of the chamber, the chamber further including glass beads and polyacrylamide beads;

loading reagent into the chamber;

rotating the chamber at a first speed of about 50 rpm and at a first time period of about one minute to mix contents of the chamber and form a mixture by activating a motor of the torque generating device and rotating the chamber about the axis of rotation of the chamber while the housing is stationary;

heating the mixture at about 37° C. for about 25 minutes with a heater included with the torque generating device to activate red blood cells of the mixture to form a clot and release thrombin;

rotating the chamber at a second speed of from about 1,500 rpm to about 3,500 rpm and at a second time period of about two minutes to cause thrombin to separate from the mixture, rise to a filter of the chamber, and pass through the filter of the chamber, and collect outside of the chamber between an inner wall of the housing and the chamber; and extracting the thrombin from within the housing through an aspiration port fixedly mounted between the chamber and an inner wall of the housing.

31. The method of claim 30, wherein the composition includes whole blood.

32. The method of claim 30, wherein the composition includes plasma.

33. The method of claim 30, further comprising loading about 24 cc of one of whole blood or plasma into the chamber.

34. The method of claim 30, wherein the chamber includes about 8 grams of class beads.

35. The method of claim 34, wherein the chamber includes about 4.5 grams of polyacrylamide beads.

36. The method of claim 30, further comprising loading about 8 cc of the reagent into the chamber, the reagent comprising calcium chloride and ethanol.

37. The method of claim 30, wherein the extracted thrombin is concentrated at from about 6× to about 7×.

38. The method of claim 30, further comprising applying the extracted thrombin to a wound site.

39. The method of claim 30, further comprising forming a second solution that includes about ten parts thrombin and about one part platelet poor plasma and applying the second solution to a wound.

40. The method of claim 39, further comprising spraying the second solution onto the wound.

41. The method of claim 30, wherein said multi-component composition includes concentrated platelet rich plasma.

* * * * *

UNITED STATES PATENT AND TRADEMARK OFFICE
CERTIFICATE OF CORRECTION

PATENT NO. : 8,187,475 B2
APPLICATION NO. : 12/399048
DATED : May 29, 2012
INVENTOR(S) : Barry F. Hecker et al.

Page 1 of 1

It is certified that error appears in the above-identified patent and that said Letters Patent is hereby corrected as shown below:

In the Specification

Column 3, line 37, "of about of" should be --of about--.

In the Claims

Column 9, line 10, Claim 17, "rpm bar" should be --rpm by--.

Signed and Sealed this
Twenty-second Day of October, 2013

Teresa Stanek Rea
*Deputy Director of the United States Patent and Trademark Office*